(12) United States Patent
Eil et al.

(10) Patent No.: US 10,729,320 B2
(45) Date of Patent: Aug. 4, 2020

(54) DETERMINING EYE SURFACE CONTOUR USING MULTIFOCAL KERATOMETRY

(71) Applicant: Novartis AG, Basel (CH)

(72) Inventors: Martin Eil, Berlin (DE); Ole Massow, Nuremberg (DE); Carsten Thomas, Nuthe-Urstromtal (DE); Sascha Birkner, Berlin (DE)

(73) Assignee: Alcon Inc. (CH)

( * ) Notice: Subject to any disclaimer, the term of this patent is extended or adjusted under 35 U.S.C. 154(b) by 0 days.

(21) Appl. No.: 15/575,500

(22) PCT Filed: Dec. 17, 2016

(86) PCT No.: PCT/IB2016/057750
§ 371 (c)(1),
(2) Date: Nov. 20, 2017

(87) PCT Pub. No.: WO2018/109537
PCT Pub. Date: Jun. 21, 2018

(65) Prior Publication Data
US 2019/0307325 A1    Oct. 10, 2019

(51) Int. Cl.
*A61B 3/14* (2006.01)
*A61B 3/10* (2006.01)
*A61B 3/02* (2006.01)
*A61B 3/00* (2006.01)
*A61B 3/107* (2006.01)
(Continued)

(52) U.S. Cl.
CPC ............ *A61B 3/107* (2013.01); *A61B 3/0025* (2013.01); *A61B 3/14* (2013.01); *G01B 11/25* (2013.01); *G01B 11/255* (2013.01)

(58) Field of Classification Search
CPC ............ A61B 3/103; A61B 3/14; A61B 3/113; A61B 3/107; A61B 3/1225; A61B 3/024; A61B 3/032; A61B 3/1015
USPC ........ 351/206, 200, 205, 209–212, 221–222, 351/239, 243, 246
See application file for complete search history.

(56) References Cited

U.S. PATENT DOCUMENTS

| 3,536,384 A | 10/1970 | Cocks |
| 5,592,246 A | 1/1997 | Kuhn et al. |
| 9,161,688 B2 * | 10/2015 | Raymond ............... A61B 3/14 |

(Continued)

FOREIGN PATENT DOCUMENTS

| WO | 2009/100866 A1 | 8/2009 |
| WO | 2009100866 A1 | 8/2009 |

*Primary Examiner* — Dawayne Pinkney
(74) *Attorney, Agent, or Firm* — Joseph Weatherbee, Esq.

(57) ABSTRACT

A system and method for determining eye surface contour using multifocal keratometry is disclosed. The system includes a light source, a light detector, a processor, a non-transitory machine-readable medium communicatively coupled to the processor, and instructions stored on the non-transitory machine-readable medium. The instructions, when loaded and executed by the processor, cause the processor to project a light, using the light source, onto a plurality of surfaces of an eye; create, using the light detector, an image of a plurality of reflections, each of the plurality of reflections created by reflecting the light off of one of the plurality of surfaces of the eye; determine that the plurality of reflections are in focus in the image; and calculate, based on the determination, a curvature of the plurality of surfaces of the eye based on the image.

18 Claims, 3 Drawing Sheets

(51) Int. Cl.
G01B 11/25 (2006.01)
G01B 11/255 (2006.01)

(56) References Cited

U.S. PATENT DOCUMENTS

| | | |
|---|---|---|
| 2001/0055095 A1* | 12/2001 | D'Souza ................ A61B 3/107 351/212 |
| 2013/0235343 A1 | 9/2013 | Lee et al. |
| 2015/0190046 A1 | 7/2015 | De Paz Sicam et al. |

* cited by examiner

DETERMINING EYE SURFACE CONTOUR USING MULTIFOCAL KERATOMETRY

TECHNICAL FIELD

The present invention generally relates to medical imaging and, in particular, to systems and methods for acquiring and processing data corresponding to the surfaces of an eye through multifocal keratometry.

BACKGROUND

Keratometry is used in medical imaging to measure the contours of a surface. For example, keratometry may be used to measure the curvature of the outer surface of the cornea of an eye. A keratometry instrument exposes the eye to a light source and measures the reflections off of the outer surface of the cornea to determine the curvature. Typically, keratometry is used to determine the contour of the outer surface of the eye and is not used to determine the contour of surfaces deeper in the eye.

SUMMARY OF THE INVENTION

In accordance with some embodiments of the present disclosure, a system for keratometry is disclosed. The system includes a light source, a light detector, a processor, a non-transitory machine-readable medium communicatively coupled to the processor, and instructions stored on the non-transitory machine-readable medium. The instructions, when loaded and executed by the processor, cause the processor to project a light, using the light source, onto a plurality of surfaces of an eye; create, using the light detector, an image of a plurality of reflections, each of the plurality of reflections created by reflecting the light off of one of the plurality of surfaces of the eye; determine that the plurality of reflections are in focus in the image; and calculate, based on the determination, a curvature of the plurality of surfaces of the eye based on the image.

In accordance with another embodiment of the present disclosure, a method for keratometry is disclosed. The method includes projecting a light onto a plurality of surfaces of an eye; creating an image of a plurality of reflections, each of the plurality of reflections created by reflecting the light off of one of the plurality of surfaces of the eye; determining that the plurality of reflections are in focus in the image; and calculating, based on the determination, a curvature of the plurality of surfaces of the eye based on the image.

The above systems may be used with the above methods and vice versa. In addition, any system described herein may be used with any method described herein and vice versa.

BRIEF DESCRIPTION OF THE DRAWING

For a more complete understanding of the present disclosure and its features and advantages, reference is now made to the following description, taken in conjunction with the accompanying drawings, in which.

DETAILED DESCRIPTION

The present disclosure provides a system and method for multifocal keratometry, allowing the curvature of multiple surfaces in an eye to be determined. Providing the curvature or topometry of multiple surfaces of an eye may more accurately determine the curvature of deeper surfaces of the eye.

Figure 1:
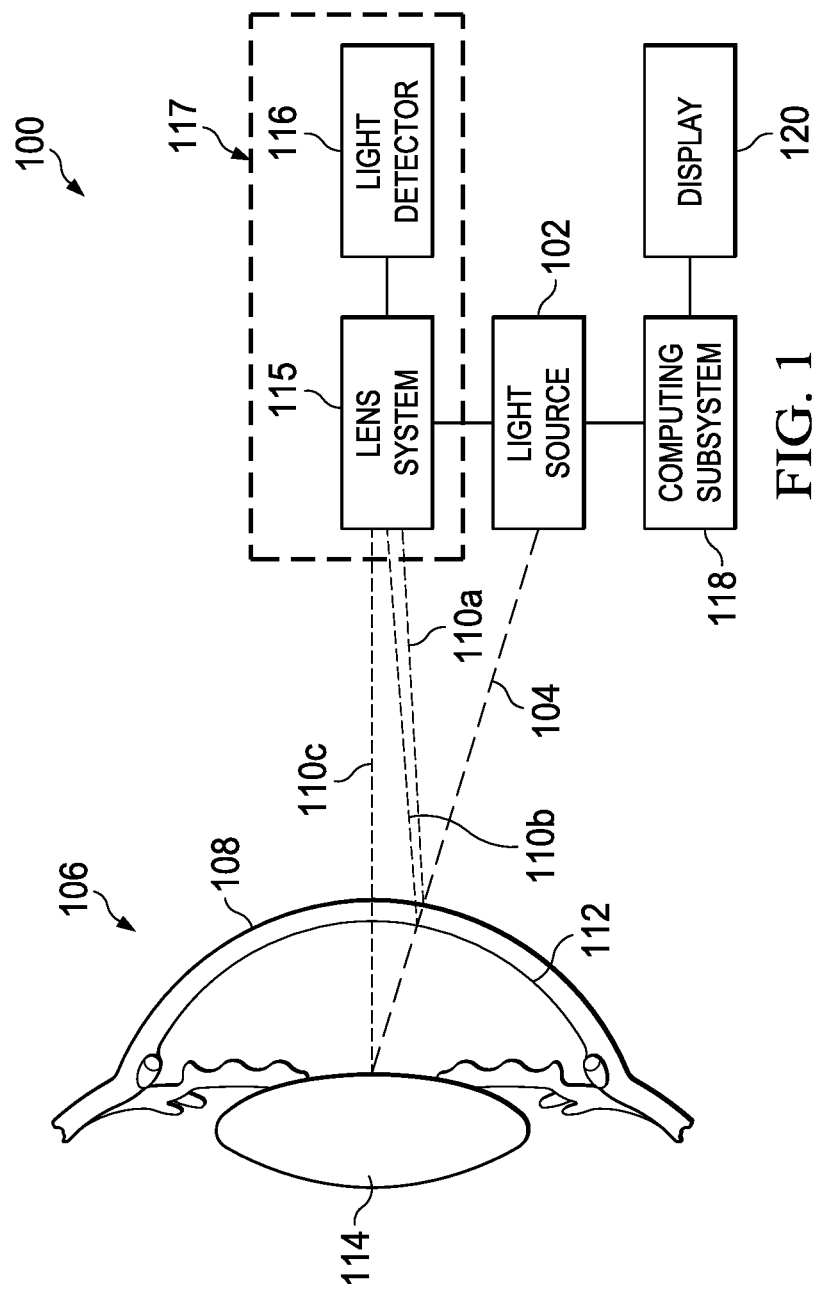
FIG. 1 is a schematic view of a system for performing multifocal keratometry including a light source, a light detector, and a computing system.
Figure 2:
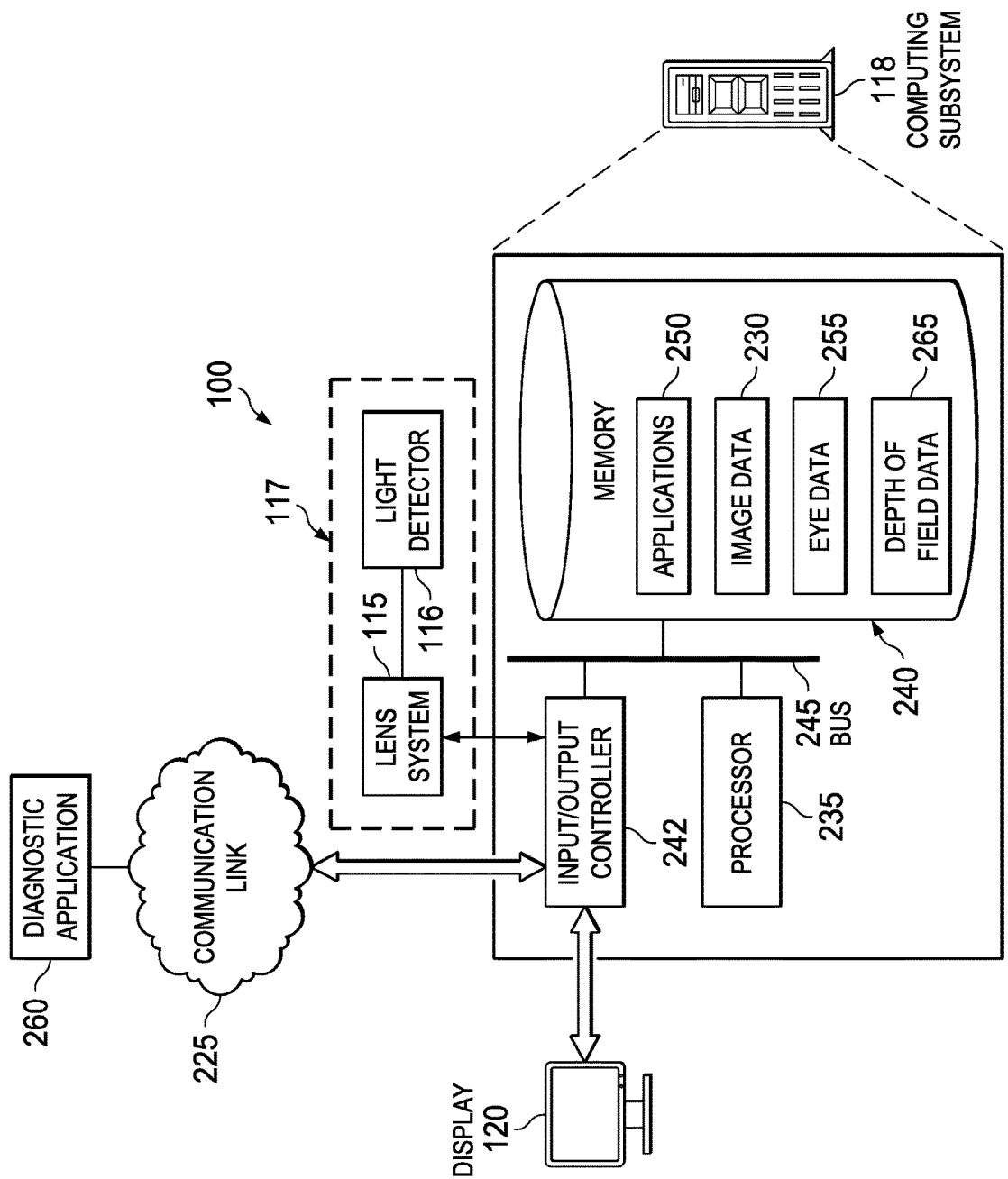
FIG. 2 is a block diagram of the computing system and display of the multifocal keratometry system shown in FIG. 1.
Figure 3:
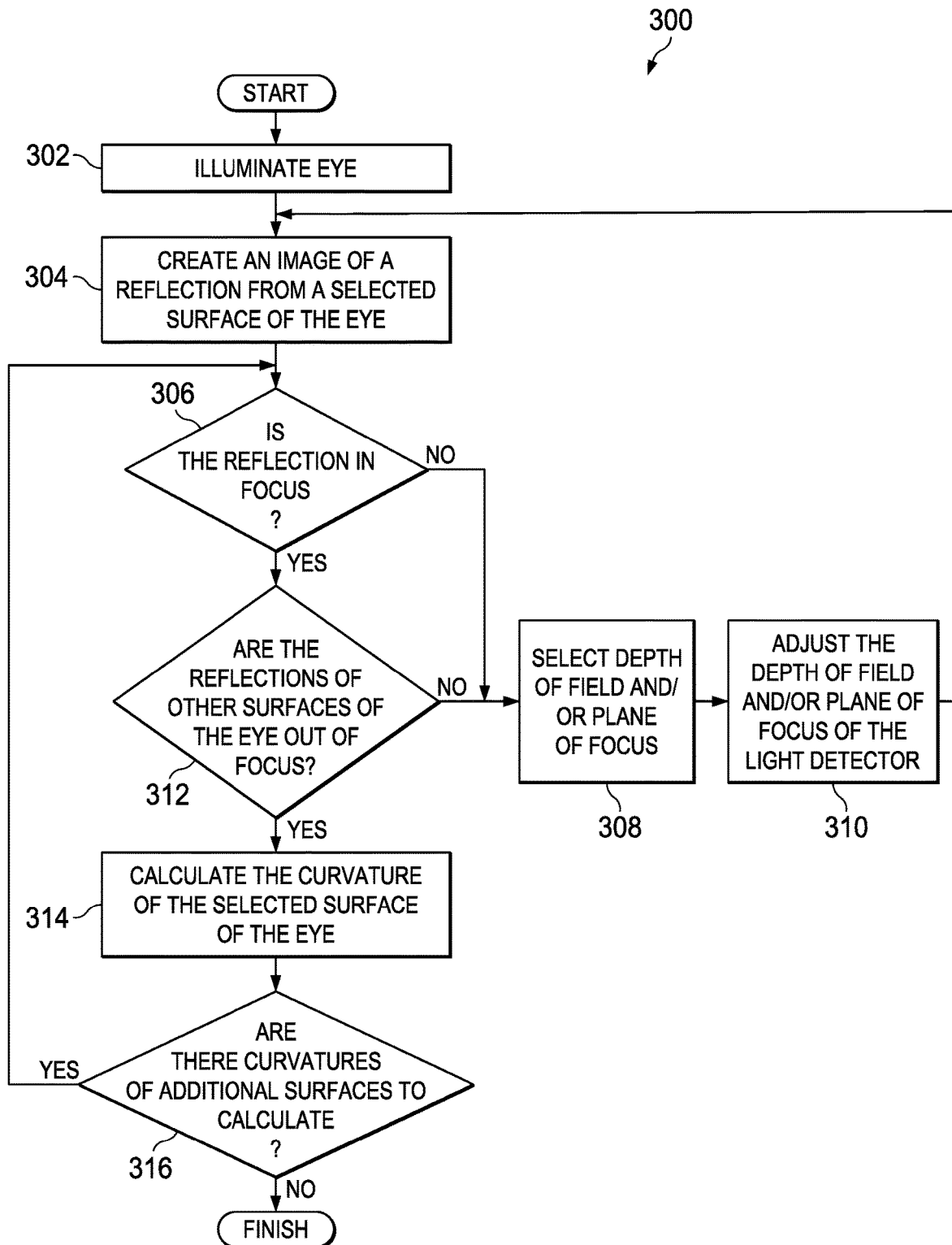
FIG. 3 is a flow chart of a method of determining the curvature of a surface of an eye.

A further description of a multifocal keratometry system, components thereof, and methods of its uses is presented with reference to FIGS. 1 through 3.

FIG. 1 is a schematic view of a system for performing multifocal keratometry including a light source, a light detector, and a computing system. Multifocal keratometry system 100 includes light source 102. Light source 102 may project light beam 104 onto eye 106. Light source 102 may create light beam 104 using any suitable light source, such as an incandescent bulb, a fluorescent bulb, a light emitting diode (LED), an infrared LED, a laser, a display, a projector, or any combination thereof. Light beam 104 may include multiple light beams arranged to project light onto eye 106 in a known pattern. For example, light beam 104 may include light beams arranged in a circular pattern such that a circular pattern of light dots appears on the different surfaces of the cornea of eye 106, such as surfaces 108, 112, 114, or any combination thereof.

When light beam 104 is projected onto eye 106, the surfaces of eye 106 act as a mirror, creating reflections 110. Each surface of eye 106 may reflect light at different angles, creating multiple reflections 110. For example, in FIG. 1, reflection 110a is the reflection of light beam 104 from anterior surface 108 of the cornea of eye 106, reflection 110b is the reflection of light beam 104 from posterior surface 112 of the cornea of eye 106, and reflection 110c is the reflection of light beam 104 from lens 114 of eye 106. The geometry, such as the surface curvature, of anterior surface 108, posterior surface 112, and lens 114 determines the angle between light beam 104 and reflections 110 as well as the size of reflections 110.

Reflections 110 may be passed through lens system 115 and detected by light detector 116. In some examples, lens system 115 may be a multifocal optical lens system having the capability of creating an image at multiple depths of focus simultaneously. In some examples, lens system 115 may be a component of monofocal optical imaging system 117 that creates multiple images at multiple depths of focus. Lens system 115 may contain additional lenses or other elements to assist with image creation. Light detector 116 may be any electronic device able to convert light to a digital image. For instance, it may be a digital camera, a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits. The operation of lens system 115 and light detector 116 is described in more detail with respect to FIG. 3.

Lens system 115 may focus reflections 110 and light detector 116 may convert reflections 110 into data to create an image of reflections 110. Light detector 116 may transfer the one or more images to computing subsystem 118. Computing subsystem 118 may perform calculations to determine the size of a given reflection 110 and thus determine the curvature of the surface of eye 106 that reflected a given reflection 110. Computing subsystem 118 is described in further detail in FIG. 2. For example, the radius of curvature of posterior surface 112 of the cornea of eye 106 may be determined using the following formula:

$$R = 2d \frac{I}{O}$$

where
R=the radius of curvature of posterior surface 112 of the cornea of eye 106;
d=the distance between posterior surface 112 of the cornea of eye 106 and light source 102;
I=the size of reflection 110; and
O=the size of posterior surface 112 of the cornea of eye 106.

FIG. 2 is a block diagram of the computing system and display of the multifocal keratometry system shown in FIG. 1. Multifocal keratometry system 100 may include lens system 115, light detector 116, computing subsystem 118, display 120, and communication link 225. Display 120 may be any suitable device used to display information to a user such as a monitor, a screen, heads-up display goggles or glasses, a projection, or any combination thereof. Multifocal keratometry system 100 may include any number of displays 120.

Imaging system 117 may include lens system 115 and light detector 116. Lens system 115 may focus one or more reflections of one or more surfaces of an eye, such as eye 106 shown in FIG. 1. Light detector 116 may detect the focused reflections and create images of one or more reflections of one or more surfaces of an eye, such as eye 106 shown in FIG. 1, by converting the reflections into data. Light detector 116 may then transmit the images to computing subsystem 118 for storage as image data 230 as discussed in further detail below. Light detector 116 may be any electronic device able to convert light to a digital image. For instance, it may be a digital camera, a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits. Lens system 115 may be a multifocal optical lens system having the capability of creating an image at multiple depths of focus simultaneously, a monofocal optical lens system that creates multiple images at multiple depths of focus, or any combination thereof. Lens system 115 may contain additional lenses or other elements to assist with light conversion. Light detector 116 produces a digital image with sufficient resolution to produce a usable image, even after image processing.

All or part of computing subsystem 118 may operate as a component of or independent of multifocal keratometry 100 or independent of any other components shown in FIG. 1. Computing subsystem 118 may include processor 235, memory 240, and input/output controllers 242 communicatively coupled by bus 245. Processor 235 may include hardware for executing instructions, such as those making up a computer program, such as application 250. As an example and not by way of limitation, to execute instructions, processor 235 may retrieve (or fetch) the instructions from an internal register, an internal cache, and/or memory 240; decode and execute them; and then write one or more results to an internal register, an internal cache, and/or memory 240. This disclosure contemplates processor 235 including any suitable number of any suitable internal registers, where appropriate. Where appropriate, processor 235 may include one or more arithmetic logic units (ALUs); be a multi-core processor; or include one or more processors 235. Although this disclosure describes and illustrates a particular processor, this disclosure contemplates any suitable processor.

Processor 235 may execute instructions, for example, to determine the curvature of a surface of an eye. For example, processor 235 may run application 250 by executing or interpreting software, scripts, programs, functions, executables, or other modules contained in application 250. Processor 235 may perform one or more operations related to FIG. 3. Input data received by processor 235 or output data generated by processor 235 may include image data 230, eye data 255, and depth of field data 265.

Memory 240 may include, for example, random access memory (RAM), a storage device (e.g., a writable read-only memory (ROM) or others), a hard disk, a solid state storage device, or another type of storage medium. Computing subsystem 210 may be preprogrammed or it may be programmed (and reprogrammed) by loading a program from another source (e.g., from a CD-ROM, from another computer device through a data network, or in another manner). Input/output controller 242 may be coupled to input/output devices (e.g., display 120, light detector 116, a mouse, a keyboard, or other input/output devices) and to communication link 225. The input/output devices may receive and transmit data in analog or digital form over communication link 225.

Memory 240 may store instructions (e.g., computer code) associated with an operating system, computer applications, and other resources. Memory 240 may also store application data and data objects that may be interpreted by one or more applications or virtual machines running on computing subsystem 118. For example, image data 230, eye data 255, depth of field data 265, and applications 250 may be stored in memory 240. In some implementations, a memory of a computing device may include additional or different data, applications, models, or other information.

Image data 230 may include information related to images created by light detector 116 that may be used to determine the curvature of the surface of an eye. Eye data 255 may include information related to the attributes of the eye. For example, eye data 255 may include the depth of one or more surfaces of an eye such as the depth of the anterior surface of the cornea, the posterior surface of the cornea, and the lens. The depths may be based on averages for a human eye or may be populated based on values of a given person. Depth of field data 265 may include depth of field settings for light detector 116 based on the values in eye data 255, as described with respect to FIG. 3. Values from image data 230, eye data 255, and depth of field data 265 may be communicated to diagnostic application 260 via communications link 225.

Applications 250 may include software applications, scripts, programs, functions, executables, or other modules that may be interpreted or executed by processor 235. Applications 250 may include machine-readable instructions for performing one or more operations related to FIG. 3. Applications 250 may include machine-readable instructions for calculating the shape of the surface of an eye. For example, applications 250 may be configured to analyze image data 230 to determine the curvature of the surface of an eye. Applications 250 may generate output data and store output data in memory 240, in another local medium, or in one or more remote devices (e.g., by sending output data via communication link 225).

Communication link 225 may include any type of communication channel, connector, data communication network, or other link. For example, communication link 225 may include a wireless or a wired network, a Local Area Network (LAN), a Wide Area Network (WAN), a private network, a public network (such as the Internet), a wireless network, a network that includes a satellite link, a serial link, a wireless link (e.g., infrared, radio frequency, or others), a parallel link, a universal serial bus (USB) link, or another type of data communication network.

Lens system 115 may focus one or more images at various depths of field, various planes of focus, or both. Light detector 116 may then record the one or more images. The images may be stored in image data 230. Processor 235 may then execute application 250 to determine the curvature of one or more surfaces of an eye based on image data 230 and eye data 255. Once application 250 identifies the curvature of one or more surfaces of the eye, application 250 may store the curvature of the surface. Processor 235 may then output the curvature of the surface to diagnostic application 260 via communications link 225. The process of determining the curvature of a surface of the eye is described in more detail in FIG. 3.

Diagnostic application 260 may be an application used to diagnose a feature of an eye, such as curvature, topography, astigmatism, keratoconus, or a model of the anterior eye. While diagnostic application 260 is shown in FIG. 2 as an application separate from computing subsystem 118, diagnostic application 260 may be stored on memory 240 and executed by processor 235.

FIG. 3 is a flow chart of a method of determining the curvature of a surface of an eye. The steps of method 300 may be performed by a person, various computer programs, models or any combination thereof, configured to control and analyze information from microscope systems, apparatuses and devices. The programs and models may include instructions stored on a computer readable medium and operable to perform, when executed, one or more of the steps described below. The computer readable media may include any system, apparatus or device configured to store and retrieve programs or instructions such as a hard disk drive, a compact disc, flash memory or any other suitable device. The programs and models may be configured to direct a processor or other suitable unit to retrieve and execute the instructions from the computer readable media. For example, the programs and models may be one of the applications in applications 250 shown in FIG. 2. For illustrative purposes, method 300 is described with respect to multifocal keratometry system 100 illustrated in FIG. 1; however, method 300 may be used to determine the curvature of a surface of an eye using any suitable multifocal keratometry system.

Method 300 may begin at step 302 where the multifocal keratometry system may illuminate an eye with a light source, such as light source 102 shown in FIG. 1. The light source may illuminate the eye with one or more beams of light projected onto the eye. The light beam may project light onto the eye in a pattern. For example, the light beam may be arranged in a circular pattern such that a circular pattern of light dots appears on the anterior surface of the cornea of the eye.

At step 304, the multifocal keratometry system may create an image of one or more reflections of the one or more beams of light that are projected on the eye at step 302. The reflections may pass through a lens system, such as lens system 115 shown in FIG. 1. The reflections may be converted into data by a light detector, such as light detector 116 shown in FIG. 1, to create an image. The reflections may be reflections created when the light beam reflects off of one or more surfaces of the eye. For example, the reflections may be a reflection of the light beam from the anterior surface of the cornea of the eye, a reflection of the light beam from the posterior surface of the cornea of the eye, a reflection of the light beam from the lens of the eye, or any combination thereof. The multifocal keratometry system may select a particular surface of the eye to determine the geometry of the selected surface. The multifocal keratometry system may store the image of the reflections in memory, such as memory 240 shown in FIG. 2. Additionally, the multifocal keratometry system may store the image in image data 230 shown in FIG. 2. The multifocal keratometry system may create any number of images of the reflections.

At step 306, the multifocal keratometry system may determine if the reflection in the image at step 304 is in focus. The reflection may be a reflection created by the surface selected in step 304. The reflection, as created by the light detector, may be unfocused in the image due to the depth of field settings of the light detector, plane of focus settings of the light detector, or any combination thereof. If the reflection is in focus, method 300 may proceed to step 312. If the reflection is not in focus, method 300 may proceed to step 308.

At step 308, the multifocal keratometry system may select the depth of field, plane of focus, or both of the lens system that will result in the image of the reflections from the surface of the eye being in focus in the image. The depth of field of the lens system is the distance between the nearest and farthest objects that appear in focus in an image. The plane of focus of the lens system is a two dimensional plane having the sharpest focus in an image created by the light detector. In order to focus the reflections, the depth of field, plane of focus, or both must be selected based on the geometry of the eye, the geometry of the multifocal keratometry system, or a combination thereof. For example, the depth of field, plane of focus, or both may be based on the distance between the light source and the surface of the eye for which the multifocal keratometry system is determining the curvature. The multifocal keratometry system may obtain information related to the geometry of the eye from a database, such as eye data 255 shown in FIG. 2. The geometry of the eye may be based on averages for a human eye or may be based on information for a particular patient. The plane of focus may be a curved plane such that the reflections from a curved surface of a surface of the eye are in focus.

At step 310, the multifocal keratometry system may adjust the depth of field, plane of focus, or both of the lens system based on the selections made at step 308. The multifocal keratometry system may adjust the imaging system by changing settings of the lens system. The reflections from multiple surfaces of the eye may be focused in a single image. For example, the lens system may contain multifocal optics capable of focusing multiple depths of focus on a single image. The depths of focus may be set based on the geometry of each surface of the eye, as described at step 308. The reflections from multiple surfaces of the eye may also be detected and created into images simultaneously using multiple lens systems and light detectors. For example, one lens system and light detector combination may have depth of field, plane of focus, or both settings to create a focused image of the reflections from the anterior surface of the cornea, a second lens system and light detector combination may have depth of field, plane of focus, or both settings to create a focused image of the reflections from the posterior surface of the cornea, and a third lens system and light detector combination may have depth of field, plane of focus, or both settings to create a focused image of the reflections from the anterior surface of the cornea. Each image may be analyzed individually to calculate the curvature of the surface of each surface of the eye. The reflections from multiple surfaces of the eye may further be shown in a series of images. For example, the lens system may be equipped with a monofocal optical lens system. The monofocal optical lens system may have an adjustable optical element, such as an adaptively focusable lens, a fluid lens, or a zoom objective lens. The lens system and light detector combination may create a series of images of the eye and adjust the depth of field, plane of focus, or both between each image. The images may be created continuously or in a step-wise manner. The multifocal keratometry system may analyze each image, at step 306, to determine which images have reflections in focus and select the images for use to calculate the curvature of a surface of the eye in step 312. Once the multifocal keratometry system adjusts the depth of field, plane of focus, or both, method 300 may return to step 304 to create another image of the reflections from the surface of the eye.

At step 312, the multifocal keratometry system may determine if reflections from surfaces of the eye that are not the surface selected in step 304 are out of focus. The reflections of the unselected surfaces may be out of focus to allow the multifocal keratometry system to identify in focus reflections from the selected surface and calculate the geometry of the selected surface in step 314. If the reflections from the unselected surfaces are not out of focus, method 300 may return to step 308. If the reflection are out of focus, method 300 may proceed to step 314.

At step 314, the multifocal keratometry system may calculate the curvature of the selected surface of the eye. The radius of curvature may be determined based on the distance between the surface and the light source, the diameter of the surface, and the diameter of the reflection according to the following formula:

$$R = 2d\frac{I}{O}$$

where
R=the radius of curvature of the surface of the eye;
d=the distance between the surface of the eye and the light source;
I=the diameter of the reflection; and
O=the diameter of the surface of the eye.

At step 316, the multifocal keratometry system may determine if there are additional surfaces of the eye for which the curvature is to be determined. If there are additional surfaces for which to calculate the curvature, method 300 may return to step 306 to determine if the reflections from the additional surface is in focus; otherwise method 300 may be complete.

Modifications, additions, or omissions may be made to method 300 without departing from the scope of the present disclosure. For example, the order of the steps may be performed in a different manner than that described and some steps may be performed at the same time. Additionally, each individual step may include additional steps without departing from the scope of the present disclosure.

Although the present disclosure has been described with several embodiments, various changes and modifications may be suggested to one skilled in the art. The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for keratometry comprising:
a light source;
a light detector, wherein the light detector includes an adaptively focusable lens;
a processor;
a non-transitory machine-readable medium communicatively coupled to the processor; and
instructions stored on the non-transitory machine-readable medium, the instructions, when loaded and executed by the processor, cause the processor to:
project, using the light source, a light onto a plurality of surfaces of an eye;
create, using the light detector, an image of a plurality of reflections, each of the plurality of reflections created by reflecting the light off of one of the plurality of surfaces of the eye, wherein each of the plurality of images are created at a different depth of focus and a different plane of focus;
determine that the plurality of reflections are in focus in the image; and
calculate, based on the determination, a curvature of the plurality of surfaces of the eye based on the image.

2. The system of claim 1, wherein the instructions further cause the processor to:
determine that the plurality of reflections are unfocused in the image;
select a depth of field at which to create a second image, the depth of field selected to focus the plurality of reflections in the second image;
determine that the plurality of reflections are in focus in the second image; and
calculate, based on the determination, a curvature of the plurality of surfaces of the eye based on the image.

3. The system of claim 1, wherein the instructions further cause the processor to:
determine that the plurality of reflections are unfocused in the image;
select a plane of focus at which to create a second image, the plane of focus selected to focus the plurality of reflections in the second image;
determine that the plurality of reflections are in focus in the second image; and
calculate, based on the determination, a curvature of the plurality of surfaces of the eye based on the image.

4. The system of claim 3, wherein selecting the plane of focus includes changing a distance between the plurality of surfaces of the eye and an imaging system.

5. The system of claim 3, wherein selecting the plane of focus includes choosing a plurality of planes of focus.

6. The system of claim 3, wherein the plane of focus is curved.

7. The system of claim 1, wherein the light detector includes a plurality of lenses.

8. The system of claim 1, wherein the plurality of images are created continuously.

9. The system of claim 1, wherein the plurality of images are created stepwise.

10. A method for keratometry comprising:
    projecting a light onto a plurality of surfaces of an eye;
    creating an image of a plurality of reflections, each of the plurality of reflections created by reflecting the light off of one of the plurality of surfaces of the eye, wherein each of the plurality of images created at a different depth of focus and a different plane of focus, and wherein the plurality of images are created using an adaptively focusable lens;
    determining that the plurality of reflections are in focus in the image; and
    calculating, based on the determination, a curvature of the plurality of surfaces of the eye based on the image.

11. The method of claim 10, further comprising:
    determining that the plurality of reflections are unfocused in the image;
    selecting a depth of field at which to create a second image, the depth of field selected to focus the plurality of reflections in the second image;
    determining that the plurality of reflections are in focus in the second image; and
    calculating, based on the determination, a curvature of the plurality of surfaces of the eye based on the image.

12. The method of claim 10, further comprising:
    determining that the plurality of reflections are unfocused in the image;
    selecting a plane of focus at which to create a second image, the plane of focus selected to focus the plurality of reflections in the second image;
    determining that the plurality of reflections are in focus in the second image; and
    calculating, based on the determination, a curvature of the plurality of surfaces of the eye based on the image.

13. The method of claim 12, wherein selecting the plane of focus includes changing a distance between the plurality of surfaces of the eye and an imaging system.

14. The method of claim 12, wherein selecting the plane of focus includes choosing a plurality of planes of focus.

15. The method of claim 12, wherein the plane of focus is curved.

16. The method of claim 10, wherein the plurality of images are created using a plurality of imaging systems.

17. The method of claim 10, wherein the plurality of images are created continuously.

18. The method of claim 10, wherein the plurality of images are created stepwise.

* * * * *